United States Patent [19]
Sun et al.

[11] Patent Number: 6,124,391
[45] Date of Patent: Sep. 26, 2000

[54] SUPERABSORBENT POLYMERS HAVING ANTI-CAKING CHARACTERISTICS

[75] Inventors: Fang Sun, Lisle, Ill.; Heather S. Jones, Greensboro, N.C.; Thomas A. Kaiser, Greensboro, N.C.; Whei-Neen Hsu, Greensboro, N.C.; Ronald L. Molen, Greensboro, N.C.; Peter A. Deaton, Greensboro, N.C.; Bernfried A. Messner, Greensboro, N.C.

[73] Assignee: Stockhausen GmbH & Co. KG, Germany

[21] Appl. No.: 09/135,844

[22] Filed: Aug. 18, 1998

[51] Int. Cl.$^7$ .................................................... C08K 3/34
[52] U.S. Cl. ............................................ 524/447; 523/223
[58] Field of Search .............................. 524/447; 523/223

[56] References Cited

U.S. PATENT DOCUMENTS

| | | | |
|---|---|---|---|
| 3,012,900 | 12/1961 | Kleinmann et al. | 117/4 |
| 3,723,153 | 3/1973 | Nagata et al. | 117/21 |
| 4,107,382 | 8/1978 | Augustine et al. | 428/368 |
| 4,286,082 | 8/1981 | Tsubakimoto et al. | 526/240 |
| 4,359,492 | 11/1982 | Schlademan | 427/222 |
| 4,381,782 | 5/1983 | Mazurak et al. | 604/368 |
| 4,448,900 | 5/1984 | Schwarz | 521/57 |
| 4,533,562 | 8/1985 | Ikegami et al. | 427/3 |
| 4,576,835 | 3/1986 | Gardenier et al. | 427/222 |
| 4,610,678 | 9/1986 | Weisman et al. | 604/368 |
| 4,734,478 | 3/1988 | Tsubakimoto et al. | 527/300 |
| 4,774,138 | 9/1988 | Gardenier et al. | 428/407 |
| 4,833,179 | 5/1989 | Young et al. | 522/183 |
| 4,880,470 | 11/1989 | Hyche et al. | 106/271 |
| 4,898,616 | 2/1990 | Hyche et al. | 106/271 |
| 4,952,650 | 8/1990 | Young et al. | 526/194 |
| 4,960,644 | 10/1990 | Hyche et al. | 428/407 |
| 4,975,120 | 12/1990 | Hyche et al. | 106/271 |
| 5,006,565 | 4/1991 | Tusim et al. | 521/57 |
| 5,007,961 | 4/1991 | Hyche et al. | 106/18 |
| 5,096,493 | 3/1992 | Hyche et al. | 106/271 |
| 5,190,579 | 3/1993 | Gose et al. | 106/18 |
| 5,200,270 | 4/1993 | Ishida et al. | 428/403 |
| 5,236,649 | 8/1993 | Hall et al. | 264/130 |
| 5,322,731 | 6/1994 | Callahan, Jr. et al. | 428/327 |
| 5,334,644 | 8/1994 | Gose et al. | 524/487 |
| 5,409,771 | 4/1995 | Dahmen et al. | 428/327 |
| 5,413,747 | 5/1995 | Akers et al. | . |
| 5,419,956 | 5/1995 | Roe | 428/283 |
| 5,443,910 | 8/1995 | Gose et al. | 428/407 |
| 5,455,288 | 10/1995 | Needham | 523/205 |
| 5,466,731 | 11/1995 | Akers et al. | . |
| 5,536,576 | 7/1996 | Hishida | 428/403 |
| 5,688,449 | 11/1997 | Fox | 264/54 |
| 5,728,742 | 3/1998 | Staples et al. | 521/57 |

FOREIGN PATENT DOCUMENTS

| | | | |
|---|---|---|---|
| 613255 | 1/1961 | Canada . | |
| 727178 | 2/1966 | Canada | 400/6 |
| 873290 | 6/1971 | Canada | 117/45 |
| 2180590 | 1/1997 | Canada | A61L 15/60 |
| 0 705 643A1 | 4/1996 | European Pat. Off. | B01J 20/32 |
| 0 755 964A2 | 1/1997 | European Pat. Off. | C08J 3/075 |
| 1200535 | 9/1965 | Germany . | |
| 56 95936 | 12/1979 | Japan . | |
| 94/22940 | 10/1994 | WIPO | C08J 3/12 |
| 97/19582 | 6/1997 | WIPO . | |

OTHER PUBLICATIONS

Buchholz, "Keeping Dry with Superabsorbent Polymers", *Chemtech,* (Sep. 1994) pp. 38–43.
"The Merck Index, an Encyclopedia of Chemicals, Drugs, and Biologicals", edited by Budavari et al. (1989).
"NeoGen™2000—Basic Formulating Tips" (Sep. 1996).
"NeoGen™DGH" (Sep. 1996).

*Primary Examiner*—Kriellion Sanders
*Attorney, Agent, or Firm*—Jenkins & Wilson, P.A.

[57] ABSTRACT

A particulate material composition of superabsorbent polymer particles, wherein less than about 60% by weight of the superabsorbent polymer particles will pass through a U.S. Standard 50 mesh sieve. The composition has anti-caking properties and also reduced dusting. The composition can be produced by mixing the superabsorbent polymer particles with an inorganic powder, such as clay.

67 Claims, No Drawings

SUPERABSORBENT POLYMERS HAVING ANTI-CAKING CHARACTERISTICS

TECHNICAL FIELD

The present invention relates, in general, to polymers that absorb aqueous liquids (such as water, blood, and urine). More particularly, the present invention relates to superabsorbent polymers, namely polymers that absorb over 20 times their weight in water, which superabsorbent polymers have unique anti-caking characteristics from admixing with a fine inorganic powder. As is well known, since superabsorbent polymers readily absorb water, the polymer particles will, during storage or during shipment to an end-use manufacturer (for instance, a manufacturer of absorbent sanitary articles, such as disposable diapers, disposable adult incontinence garments, disposable sanitary napkins, and disposable bandages, or a manufacturer of water blocking tapes placed inside a cable along with fiber optic filaments) take on moisture from the ambient surroundings in a humid environment and cake, i.e., the polymer particles will agglomerate together into a large mass. The superabsorbent polymer compositions of the present invention obviate this caking problem.

DEFINITIONS OF ABBREVIATIONS

The following abbreviations are employed throughout this specification.

| Abbreviation | Definition |
| --- | --- |
| SAP | superabsorbent polymer, a polymer that absorbs over 20 times its weight in water |
| X-linking | cross-linking |
| precursor SAP | a SAP that is not surface X-linked |
| CRC | centrifuge retention capacity |
| AUL | absorbency under load |
| psi | pounds per square inch |
| mg | milligram |
| ppm | parts per million |
| mm | millimeter |
| cm | centimeter |
| μm | micrometer |
| NaOH | sodium hydroxide |
| PEG | polyethylene glycol |
| PSD | particle size distribution |
| hr | hour |
| wt | weight |
| RH | relative humidity |

BACKGROUND OF THE INVENTION

SAPs, namely highly water-swellable polymers, typically are prepared by solvent or solution polymerization of an aqueous mixture of monomers. Usually, one or more X-linking agents are incorporated into the monomer mixture. When the polymerization has ended, the resultant is dried and subjected to mechanical grinding to create a desired particle size distribution for the particulate SAP.

As noted above, SAPs are useful in various absorbent articles, due to the ability of the SAPs to absorb bodily liquids in a ready manner. However, SAPs also absorb water from the air, and when exposed to humid environments, tend to agglomerate together into a large mass, i.e., to cake. Consequently, the SAP particles are not free-flowing.

Problems arise when SAP particles are not free-flowing. For instance, the particles are difficult to incorporate into absorbent articles because the reduced flowability interferes with the uniform distribution of the particles within an absorbent core. Additionally, the particles tend to stick to each other and to the manufacturing equipment, such as screens, driers, and fabricating machinery. Thus, production must be periodically stopped so that the equipment can be cleaned by removing the agglomerated particles. Finally, if the particles have already absorbed some water and agglomerated, then the water-swelling capacity of the end use absorbent article will be decreased.

Various attempts have been made to reduce the caking tendencies of SAPs. One way has been by blending SAP particles with silica. For instance, U.S. Pat. No. 4,734,478 (issued Mar. 29, 1988) to Tsubakimoto, Shimomura, Irie, Masuda, Kimura, and Hatsuda, assignors to Nippon Shokubai Kagaku Kogyo, shows mixing 0.01 to 10 parts by weight of finely divided silica with 100 parts by weight of superabsorbent polymer. Also, WO 94/22940 (published Oct. 13,1994) to Staples, Wood, and Treptow, assignors to Dow Chemical, shows mixing less than 10% by weight of fumed silica with superabsorbent polymer. Additionally, U.S. Pat. No. 5,419,956 (issued May 30, 1995) to Roe, assignor to The Proctor & Gamble Company, shows an absorbent end use article that includes very small SAP particles (at least 70% by weight will pass through a U.S. Standard 50 mesh sieve which has openings of 300 μm in size) that are formed by solution polymerization and that are mixed with amorphous silica. It is noted that silica occurs naturally as quartz, sand flint, and agate.

Surfactants also have been used in attempts to reduce the tendency of superabsorbent polymer particles to agglomerate, as shown for instance, in both U.S. Pat. No. 4,286,082 (issued Aug. 25, 1981) to Tsubakimoto, Shimomura, Irie, and Masuda, assignors to Nippon Shokubai Kagaku Kogyo, and U.S. Pat. No. 4,381,782 (issued May 3, 1983) to Mazurak and Fries, assignors to Kimberly-Clark. However, surfactants can also reduce the surface tension of the superabsorbent polymer, which, in turn, interferes with the ability of the polymer to absorb and to hold liquid.

Of additional interest in connection with various other compounds used in attempts to reduce the tendency of superabsorbent polymers to agglomerate are the following. U.S. Pat. No. 5,728,742 (issued Mar. 17, 1998) to Staples, Henton, Rose, and Fialkowski, assignors to Dow Chemical, shows quaternary ammonium salts. Canadian Patent No.2, 180,590 (issued Jan. 8, 1997) to Engelhardt, Stuven, Daniel, and Herfert, assignors to Hoechst Aktiengefellfchaft, shows wax. Also, European Published Patent Application No. 0 705 643 A1 (published Apr. 10, 1996) to Sumlya, Koike, and Tanaka, assignors to Sanyo Chemical, shows silicone oil.

Lastly, the following are of interest in connection with general background information vis-a-vis well known procedures for the manufacture of SAPs.

The journal article "Keeping Dry with Superabsorbent Polymers", *Chemtech*, (September, 1994) by Buchholz, contains an excellent discussion of conventional methods for making SAPs, as well as various uses for SAPs, such as in the above-noted sanitary articles (i.e., diapers, incontinence garments, etc.), in a sealing composite between concrete blocks that make up the wall of underwater tunnels, and in tapes for water blocking in fiber optic cables and power transmission cables.

A good discussion of the methods for making SAPs can also be seen in U.S. Pat. No. 5,409,771 (issued Apr. 25, 1995) to *Dahmen and Mertens*, assignors to Chemische Fabrik Stockhausen GmbH. More specifically, this patent mentions that commercially available SAPs are generally X-linked polyacrylic acids or X-linked starch-acrylic-acid-graft-polymers, the carboxyl groups of which are partially neutralized with sodium hydroxide or caustic potash. Also mentioned is that the SAPs are made by two methods, namely the solvent or solution polymerization method and the inverse suspension or emulsion polymerization method.

In the solvent or solution polymerization method, an aqueous solution, for instance of partially neutralized acrylic acid and a multi-functional network X-linking agent, is converted to a gel by radical polymerization. The resultant is dried, ground, and screened to the desired particulate size.

On the other hand, in the inverse suspension or emulsion polymerization method, an aqueous solution, for instance of partially neutralized acrylic acid, is dispersed in a hydrophobic organic solvent by employing colloids or emulsifiers, and polymerization is started by radical initiators. Water is azeotropically removed from the reaction mixture after completion of polymerization, followed by filtering and drying the resultant product. Network X-linking may be accomplished by dissolving a polyfunctional X-linking agent in the monomer solution.

The disclosures of all patents and published patent applications that are mentioned are incorporated by reference.

SUMMARY AND OBJECTS OF THE INVENTION

A need still exists for SAP compositions with good anti-caking properties. A great advantage would be given to industry to provide SAP compositions that do not agglomerate when exposed to a humid environment, i.e., which comprise preferably about 90% or more free-flowing particles, as measured by the anti-caking property test as defined below.

Therefore, the present invention provides a particulate material composition comprising an inorganic powder intermixed with particles of superabsorbent polymer. The polymer particles are of such size that less than about 60% of said polymer particles, by weight, will pass through a U.S. Standard 50 mesh sieve with 300 micrometer openings. The resultant particulate material composition exhibits excellent anti-caking characteristics, as measured by the anti-caking property test as defined below.

Also, the present invention provides a method for providing anti-caking characteristics to SAP particles. The method comprises (A) providing SAP particles of such size that less than about 60% of the polymer particles, by weight, will pass through a U.S. Standard 50 mesh sieve with 300 micrometer openings, (B) mixing an inorganic powder with the polymer particles in an amount of between about 0.2% and about 10% by weight of the polymer particles, to create a particulate material composition, and (C) achieving anti-caking characteristics in that more than about 90% of the composition particles, by weight, will pass through a U.S. Standard 12 mesh sieve with 1700 micrometer openings after at least about 3 hours at about $36 \pm 3°$ C. and about $77 \pm 3\%$ RH.

Additionally, the present invention provides an absorbent article comprising a particulate material composition. The particulate material composition comprises an inorganic powder intermixed with particles of superabsorbent polymer, said polymer particles being of such size that less than 60% of said polymer particles, by weight, will pass through a U.S. Standard 50 mesh sieve with 300 micrometer openings.

Furthermore, the present invention provides a method for providing anti-caking characteristics to a particulate material composition in an absorbent article. The method comprises (A) providing SAP particles of such size that less than about 60% of the polymer particles, by weight, will pass through a U.S. Standard 50 mesh sieve with 300 micrometer openings, (B) mixing an inorganic powder with the polymer particles in an amount of between about 0.2% and about 10% by weight of the polymer particles to create the particulate material composition, (C) achieving anti-caking characteristics in that more than about 90% of the composition particles, by weight, will pass through a U.S. Standard 12 mesh sieve with 1700 micrometer openings after at least about 3 hours at about $36 \pm 3°$ C. and about $77 \pm 3\%$ RH, and (D) forming an absorbent article from the particulate material composition of step (C). Forming the absorbent article in step (D) may be achieved by mixing the particulate material composition with a fibrous component to make a core composite, and then, using the core composite to make the absorbent article.

Accordingly, it is an object of the present invention to provide a particulate material composition of inorganic powder and SAP that obviates caking problems.

Moreover, it is an advantage of the present invention that the particulate material composition can be stored and shipped, even in hot, humid locations, such as the southern part of the United States in the summertime, or tropical locations at or near the equator, with little or no caking problems.

It is a further advantage of the present invention that the particulate material composition can obviate caking problems, yet employ SAP particles that are of typical, regular particle size distribution, rather than small particles as in the above-noted U.S. Pat. No. 5,419,956.

Another advantage of the present invention is that dust reduction properties, in addition to anti-caking properties, may be imparted to the particulate material composition with treatment of the SAP with only one agent.

Some of the objects and advantages of the invention having been stated, other objects and advantages will become evident as the description proceeds, when taken in connection with the Laboratory Examples described below.

DETAILED DESCRIPTION OF THE INVENTION

A mixture of SAP particles and inorganic powder is referred to as a "particulate material composition". For the present invention, the particulate material composition comprises particles of SAP material intermixed with small amounts of inorganic powder. The particles of SAP are generally of typical, regular PSD, by which is meant that less than about 60% by weight of the particles will pass through a U.S. Standard 50 mesh sieve (the sieve openings are 300 $\mu$m). Preferably, less than about 50% by weight will pass through a U.S. Standard 50 mesh sieve, and more preferably, less than about 40% by weight will pass through a U.S. Standard 50 mesh sieve, and even more preferably, less than about 30% by weight will pass through a U.S. Standard 50 mesh sieve.

The SAPs according to the present invention may be manufactured on a large scale by continuous or discontinuous processes. More specifically, the particulate SAP of use in the present invention may be manufactured by any of the prior art processes for making SAPs. For instance, the SAP may be made by the solvent polymerization technique or may be made by the inverse suspension or emulsion polymerization technique, which are well known techniques as discussed above.

Thus, the SAP may be obtained by polymerizing at least about 25%, more preferably about 55 to about 99.9% by weight of monomers having olefinically-unsaturated carboxylic and/or sulfonic acid groups. Such acid groups include, but are not limited to, acrylic acids, methacrylic acids, 2-acrylamido-2-methylpropane sulfonic acid, and mixtures thereof. The acid groups are present as salts, such as sodium, potassium, or ammonium salts.

The acid groups are typically neutralized to at least about 25 mol %. Preferably, the extent of neutralization is to at least about 50 mol %. More particularly, the preferred SAP has been formed from X-linked acrylic acid or methacrylic acid, which has been neutralized to an extent of about 50 to about 80 mol %. Suitable neutralizing agents are hydroxides and/or carbonates of alkaline earth metals and/or alkali metals, for instance, NaOH.

Additional useful monomers for making the SAPs include from above 0 up to about 40% by weight of acrylamide, methacrylamide, maleic acid, maleic anhydride, esters (such as hydroxyethyl acrylate, hydroxypropyl acrylate, hydroxypropyl methacrylate, and dimethyl-aminoalkyl-methacrylate), dimethyl-aminopropyl acrylamide, and acrylamidopropyl trimethylammonium chloride. Percentages below about 40% of these monomers are desirable as percentages above 40% typically will have a detrimental effect and deteriorate the swell capacity of the resultant SAP. A preferred amount is from about 1% to about 25% by weight, and more preferably from about 2% to about 10% by weight.

Suitable network X-linking agents useful in making the SAPs are those which have at least two ethylenically unsaturated double bonds, those which have one ethylenically unsaturated double bond and one functional group reactive toward acid groups, and those which are multi-functional, i.e., have several functional groups reactive toward acid groups. Suitable kinds of network X-linking agents include, but are not limited to, acrylate and methacrylate of polyols (such as butanediol diacrylate, hexanediol dimethacrylate, polyglycol diacrylate, trimethylolpropane triacrylate, allyloxy polyethylene glycol methacrylate, and ethoxylated trimethylolpropane triacrylate), allyl acrylate, diallyl acrylamide, triallyl amine, diallyl ether, methylenebisacrylamide, glycerol dimethacrylate, N-methylol methacrylamide, and N-methylolacrylamide. Suitable kinds of network X-linking agents that are multifunctional include, but are not limited to, alcohols, amines, and epoxides, such as glycol, propylene glycol, glycerol, ethylene diamine, hexamethylene diamine, glycerol polyglycidal ether, and resorcinol diglycidal ether. These network X-linking agents are distinguished from and not to be confused with the surface X-linking agents discussed below.

Furthermore, depending on the desired end use, the SAP may have a water-soluble polymeric component. The content may range from above 0 up to about 30% by weight of a component that includes, but is not limited to, partially or complete saponified polyvinyl alcohol, polyvinyl pyrrolidone, starch, starch derivatives, polyglycols, polyacrylic acids, and combinations thereof. The molecular weight of the component is not critical, provided that it is water-soluble. Preferred water-soluble polymeric components are starch, polyvinyl alcohol, and mixtures thereof. Preferably, the content of the water-soluble polymeric component in the SAP ranges from about 1 to about 5% by weight, especially if starch and/or polyvinyl alcohol are present as the water-soluble polymeric component. Also, the water-soluble polymeric component may be present as a graft polymer having the acid-groups-containing polymer.

In connection with the particle shape of the SAP, there are no specific limitations. The SAP may be the dried resultant obtained either by inverse or suspension polymerization, or by solvent or solution polymerization. A typical particle size distribution ranges between about 20 and about 2000 micrometers, preferably between about 40 and about 890 micrometers, and more preferably between about 90 and about 850 micrometers.

As is known from the above-discussed U.S. Pat. No. 5,409,771, coating a particulate SAP with an alkylene carbonate followed by heating to effect surface X-linking often improves the AUL characteristics of the SAP. An AUL property at 0.9 psi (60 g/cm$^2$) of at least about 13 grams of aqueous saline (0.9% by weight NaCl in water) per gram of SAP is desirable, especially when the end use of the SAP is in a sanitary article, such as a disposable diaper, that is subjected to pressure from the person wearing the article.

Thus, the SAPs of the present invention may be optionally coated with a surface X-linking agent, such as a diol, a diamine, a diepoxide, or an alkylene carbonate, followed by heating to effect surface X-linking. Thus, at least a portion of the SAP particles preferably is surface X-linked.

More specifically, as described in U.S. Pat. No. 5,409,771, in order to coat the particulate SAP with a surface X-linking agent, the polymer may be mixed with an aqueous-alcoholic solution of the alkylene carbonate surface X-linking agent. The following may be used as alkylene carbonates, e.g., 1,3-dioxolan-2-one, 4-methyl-1,3-dioxolan-2-one, 4,5-dimethyl-1,3-dioxolan-2-one, 4,5-dimethyl-1,3-dioxolan-2-one, 4-ethyl-1,3-dioxolan-2-one, 4-hyd roxyethyl-1,3-dioxolan-2-one, 1,3-dioxan-2-one, 4-methyl-1,3-dioxan-2-one, 4,6-dimethyl-1,3-dioxan-2-one, 1,3-dioxepan-2-one, and combinations thereof. Preferred alkylene carbonates are 1,3-dioxolan-2-one and 4-methyl-1,3-dioxolan-2-one. The amount of alcohol is determined by the solubility of the alkylene carbonate and is kept as low as possible for technical reasons, for instance, protection against explosions. Suitable alcohols are methanol, ethanol, butanol, or butyl glycol, as well as mixtures of these alcohols. The preferred solvent is water which typically is used in an amount of 0.3 to 5.0% by weight, relative to the particulate SAP. In some instances, the alkylene carbonate surface X-linking agent is dissolved in water, without any alcohol. It is also possible to apply the alkylene carbonate surface X-linking agent from a powder mixture, for example, with an inorganic carrier material, such as $SiO_2$, (see, lines 51–54 of column 4 of U.S. Pat. No. 5,409,771).

To achieve the desired surface X-linking properties, the surface X-linking agent has to be distributed evenly on the particulate SAP. For this purpose, mixing is effected in suitable mixers, such as fluidized bed mixers, paddle mixers, milling rolls, or twin-worm-mixers. It is also possible to carry out the coating of the particulate SAP with a surface X-linking agent during one of the process steps in the production of the particulate SAP. An especially suitable process for this purpose is the inverse suspension polymerization process.

According to U.S. Pat. No. 5,409,771, the thermal treatment which follows the coating treatment is carried out as follows. In general, the thermal treatment is at a temperature between 150 and 300° C. However, if the preferred alkylene carbonates are used, then the thermal treatment is at a temperature between 180 and 250° C. The treatment temperature depends on the dwell time and the kind of alkylene carbonate. At a temperature of 150° C., the thermal treatment is carried out for several hours. On the other hand, at a temperature of 250° C., a few minutes, e.g., 0.5 to 5 minutes, are sufficient to achieve the desired surface X-linking properties. The thermal treatment may be carried out in conventional dryers or ovens. Examples of dryers and ovens include rotary kilns, fluidized bed dryers, disk dryers, or infrared dryers.

The fine inorganic powder useful in the present invention may comprise any of the clays (i.e., hydrated aluminum silicates, generally of the formula $H_2Al_2Si_2O_8 \cdot H_2O$). Suitable clays are kaolin clays, such as those sold by Dry Branch Kaolin Company under the trade name NeoGen DGH (median particle size of 0.6 $\mu$m) and NeoGen 2000 (median particle size of 0.7 $\mu$m).

The average size of the particles of the inorganic powder is preferably less than about 5 $\mu$m, more preferably less than about 3 $\mu$m, and even more preferably less than about 0.8 $\mu$m. This means that some particles may be as large as 10 or 15 $\mu$m, or even larger. The size of the particles of the inorganic powder can be measured by any accurate and reliable means.

The inorganic powder is preferably mixed with the SAP particles in an amount sufficient to achieve anti-caking characteristics (at the test conditions of temperature, RH, and time, described further below). Typically, this is an amount of between about 0.2% to about 10%, more preferably about 0.5% to about 7%, and even more preferably about 0.9% to about 5.5% (i.e., between about 0.9 to about 5.5 parts of inorganic powder per 100 parts) by weight of the SAP particles. The inorganic powder may be mixed with the particles of SAP in a substantially dry state, or with the addition of a liquid such as water, in amounts typically of up to about 10 parts by weight of the liquid to 100 parts by weight of the SAP particles.

The inorganic powder and the particles of SAP can be intermixed in any suitable manner. Suitable manners include, but are not limited to, physical intermixing employing the above-described mixers that are employed for the optional surface X-linking agent. Thus, if surface X-linking is going to be effected, (1) the inorganic powder may be mixed with the precursor SAP particles prior to mixing and heating with the surface X-linking agent, or (2) the precursor SAP particles may be mixed and heated with the surface X-linking agent followed by mixing with the inorganic powder.

The inventive particulate material compositions (of the SAP particles and the inorganic powder) may be employed for any traditional use for which SAPs are employed. For instance, such uses include, but are not limited to, use in an absorbent article such as a sanitary article (i.e., diapers, incontinence garments, etc.), a sealing composite between concrete blocks that make up the wall of underwater tunnels (such as the Channel Tunnel connecting England and France, as mentioned in the above-noted *Buchholz* journal article), a tape or sheet for water blocking in fiber optic cables and power transmission cables (as also mentioned in the above-noted *Buchholz* journal article), a carrier (for insecticides, herbicides, and/or pesticides), and an agricultural material (such as STOCKOSORB®, which is a SAP marketed by Stockhausen for use in agricultural fields to improve the capability of soils to keep water and nutrients near or with the roots of plants).

The liquid acquisition time is very acceptable (see, Example 14, Comparative Example 15, and Table C below) for such absorbent articles incorporating the inventive particulate material composition and there is no need to attempt to speed up the time by reducing the average size of the SAP particles in the product, as was done in the above-noted U.S. Pat. No. 5,419,956. Hence, the present invention obviates the well known problem that when very small particles of SAP swell upon contact with liquids, the particles, when incorporated with fiber, tend to be easily forced into the interfiber capillaries. Then, the small swollen particles form a mass of coagulated gel held together by fluid surface tension-forces, thus forming a gel barrier, and resistance to fluid through flow is increased as fluid flow channels are blocked by the gel mass, resulting in a marked decrease in permeability.

To characterize the particulate material compositions (of inorganic powder and SAP) as set out in the Laboratory Examples below (both those compositions of the present invention, as well as those comparison compositions), the centrifuge retention capacity (CRC), the absorbency under load (AUL), the dust rating, the anti-caking characteristics, the acquisition time, and the rewet were measured in the following manner.

CRC. The test was conducted at ambient conditions of temperature. The particulate material compositions' retention was determined according to the tea bag test method and reported as an average value of two measurements. Approximately 200 mg of particulate material composition (of inorganic powder and SAP), that had been sieved to a particle size distribution of about 300 to 600 micrometers (not the indicated particle sizes in the Examples below), were enclosed in a tea bag and immersed in 0.9% by weight NaCl solution for 30 minutes. Then, the tea bag was centrifuged at 1600 rpm for 3 minutes (centrifuge diameter was about 18 cm) and weighed. Two tea bags without any composition were used as blanks.

Then, the CRC was calculated according to the following equation.

$$CRC = (W_3 - W_2 - W_1)/W_1$$

where:
CRC=Retention after an immersion time of 30 minutes (g of liquid absorbed/g of composition of inorganic powder and SAP); the resultant CRC value should be rounded to 2 significant figures
$W_1$=Initial weight of composition of inorganic powder and SAP (g)
$W_2$=Weight of the average blank tea bags (without composition of inorganic powder and SAP) after centrifugation (g)
$W_3$=Weight of the tea bag with composition of inorganic powder and SAP after centrifugation (g).

AUL. The test was conducted at ambient conditions of temperature. The particulate material compositions' absorbency of a 0.9% by weight NaCl solution (20±2° C.) under load was determined as follows.

The equipment used was a petri dish (diameter=150 mm; height=20 mm), fritted disc (catalogue no.9520001223 from Kontes Glass), Whatman No. 3 round filter paper, a plastic spacer (weight=5.20±0.015 g), a stainless steel weight (weight=315.3±0.09 g), an analytical balance (accuracy to 0.001 g), a stopwatch, a plexiglass cylinder with beveled edges (diameter=25 mm; height=33 mm), and a screen filter cloth (400 mesh=36 $\mu$m) on the bottom of the cylinder. The combined diameter of the spacer and the weight=24±1 mm.

After allowing the fritted disc to soak in the NaCl solution for a minimum of 1 hour just prior to test use, the fritted disc was placed in the petri dish. Then, NaCl solution was added to the petri dish so that the solution was slightly below the top of the fritted disc. Next, the Whatman filter paper was placed on top of the fritted disc, with thorough wetting of the filter paper with the NaCl solution, avoiding any supernatant liquid.

The cylinder was tared on the analytical balance. An initial weight of 0.160±0.005 g of the composition of inorganic powder and SAP was distributed onto the filter screen in cylinder bottom. The composition sample actual weight was recorded (SA).

The plastic spacer and then the stainless steel weight were carefully placed into the cylinder. The weight of the completed AUL apparatus was recorded (A). The stainless steel weight exerted a pressure load of 60 g/cm$^2$. (It is noted 60 g/cm$^2$=0.9 psi.)

Then, the AUL apparatus was placed on the wet filter paper, allowing the composition to absorb the NaCl solution for 1 hour. During the entire test, the level of NaCl solution was maintained to be slightly below the top surface of the fritted disc.

After the 1 hour, the apparatus with the swollen composition was re-weighed, and the weight recorded (B). The grams of the NaCl solution that had been retained was calculated according to the following equation.

$$AUL=(B-A)/SA$$

where,

AUL is in g/g at 0.9 psi; the resultant AUL value should be rounded to 2 significant figures A is weight in g of AUL apparatus with composition prior to absorbing NaCl solution B is weight in g of AUL apparatus with composition after absorbing NaCl solution for 1 hour SA is actual weight in g of composition.

Dust rating. The test was conducted at ambient conditions of temperature.

Standards were prepared in the following manner. A 700 g sample of a superabsorbent polymer that had no anti-dusting nor flow-enhancing treatment was obtained. From this sample, 150 g was separated and placed inside of a 16 ounce (0.48 liter) French Square bottle (sold by Baxter Scientific as order no. B751 9-530S). The bottle with the 150 g sample was labeled as dusting standard no. 4.

The remaining 550 g of the sample was sieved for 2 hours using (A) a Ro-tap sieving machine, (B) screens having from top to bottom the respective ASTME-11 specification nos. 50, 170, and 325, and (C) a catch pan.

For dusting standard no. 3, all of the sample remaining in the sieves was mixed together, followed by weighing a 149.8 g portion into another French Square bottle. Then, 0.2 g of the fines from the catch pan was weighed and placed in the bottle, followed by mixing, and then sealing and labeling the bottle.

For dusting standard no. 2, weighed was a 149.9 g portion of the mixture from the sieves, which was placed in another French Square bottle. Then, 0.1 g of the fines from the catch pan was weighed and added to the bottle, followed by mixing. The bottle was then sealed and labeled.

For dusting standard no. 1, a 150.0 g portion of the mixture from the sieves was weighed and placed inside another French Square bottle. Then, the bottle was sealed and labeled.

Samples of the various compositions of inorganic powder and SAP from certain of the Examples below were prepared as follows for comparison with the four bottles of dusting standards. A 150 g portion of the sample was weighed into a French Square bottle, followed by sealing the bottle by attaching the end cap. The technician then held the sample bottle and one of the standard bottles side-by-side by the cap end of each of the bottles, faced a dark background, pointed both bottles at the ground at a 45° angle, and then in one swift motion, brought both bottles up to a vertical position with the bottom of each of the bottles directed upward. This was repeated so that the sample was compared with each of the four standard bottles, in order to determine which of the four standard bottles was most comparable to the sample. The technician then recorded the number (dusting standard no. 1, 2, 3, or 4) that the technician subjectively believed was most comparable to the sample, with a rating of 4 being the most dusty and a rating of 1 being the least dusty.

As can be seen from the Examples below, many of the samples of the inventive compositions (of kaolin+SAP) exhibited an excellent dust rating of 1.

Anti-caking. The test employed here was a variation of the anti-caking test described at lines 13–41 of column 4 of the above-noted U.S. Pat. No. 5,728,742.

More specifically, the anti-caking characteristics of the particulate material compositions (of inorganic powder and SAP) were determined by the weight % of the composition that passed through a sieve having certain size openings after exposure of the composition to a specified temperature and relative humidity for a period of time. In other words, the test procedure allows for determination of the amount of moisture the particles may absorb, yet still be free-flowing.

Samples of the various particulate material compositions were subjected to a temperature and relative humidity for the anti-caking tests of 36±3° C. and 77±3% RH, for 4 respective time periods of 3, 6, 15, and 24 hours, each ±0.25 hour. The temperature and RH were maintained by placing samples inside a controlled climate environmental chamber sold under catalog no. 700 ADH FTX, serial no. 493-001 by Lab-Line Instruments of Melrose Park, Illinois. The high temperature and high RH simulate ambient conditions for locations that have a hot, humid climate.

Respective plastic dishes, each of approximately 60 mm in diameter, were each weighed precisely on a tared balance accurate to 0.10 g. This weight was recorded as the cup weight. A 6±0.25 g sample of each particulate material composition was spread evenly in each respective plastic dish. Each respective dish with a sample was then placed in the chamber at the specified temperature and RH, for the particular exposure time.

After the particular exposure time in the chamber, the dish with the hydrated sample was removed and immediately weighed. This weight was recorded as the final weight.

Then, a large, plastic weigh boat or weigh paper was tared on the balance, followed by placing over the boat a clean, dry U.S. Standard 12 mesh sieve (or Tyler equivalent) with openings of 1700 $\mu$m in size. The hydrated sample was then slowly poured out of the dish and through the sieve.

The portion of the sample that passed through the sieve and collected in the boat was weighed. This weight was recorded as the through weight, and compared to the original amount of the sample.

The % of the particulate material composition that passed through the openings of 1700 $\mu$m, i.e., the % that was free-flowing, was recorded for anti-caking performance according to the following equation.

$$\text{\% Anti-caking}=(\text{Through Weight})/(\text{Final Weight}-\text{Cup Weight})\times 100$$

The resultant anti-caking % should be rounded to 2 significant figures, unless, of course, the sample passes by 100%.

For a particular exposure time, a passing anti-caking performance % for a sample of a particulate material composition is about 70% or higher, more preferably about 85% or higher, even more preferably about 90% or higher, and most preferably about 95% or higher.

More specifically, if a sample passed the test conditions for 3 hours, but not for any of the other time periods, the sample is considered as having light anti-caking properties. The sample is considered as having moderate anti-caking properties, if it passed the test conditions for 6 hours, but not the 15 and 24 hour time periods. If a sample passed the test conditions for 15 hours, but not for 24 hours, the sample is considered as having heavy anti-caking properties. If a sample passed the test conditions for 24 hours, it is considered as having very heavy anti-caking properties. As can be seen from Table A below, all samples passed the light test (3 hours) with better than 95%, and most samples passed the very heavy test (24 hours) with better than 70%.

Acquisition Time and Rewet (for core of SAP and cellulose).

The acquisition time is the time between the addition of liquid and its complete infiltration into each respective core. Each core was weighed and placed on a body-shaped test apparatus, and subjected to a load of 12.5 kg. An insult amount of 100 ml of 0.9% saline was added to the surface of each core through a bore hole in the test apparatus. A timer was used to determine the acquisition time. Next, there was a 20 minute waiting period. After the 20 minute waiting period, the weights were removed, and any leakage during the test was recorded.

The rewet is the amount of liquid release onto filter paper from the surface of each respective core under a predetermined pressure. In order to evaluate the rewet, each core was taken off the test apparatus, placed on the counter top, and fastened down with tape. Then, 3 pre-weighed stacks of filter paper (40 g each) and 3 weights (1270 g each) were placed on each core for 10 minutes. At the end of the specified 10 minute time, the filter paper stacks were removed and re-weighed in order to determine the rewet of the core. The resultant rewet value should be rounded to the tenths place.

The article was placed back on the body-shaped test apparatus, and the above procedure was repeated 2 additional times.

LABORATORY EXAMPLES

In the following examples, each percentage recited was a weight % unless specifically indicated otherwise as a mol %. For Examples 1–8, a commercially available surface X-linked particulate SAP sold by Stockhausen under the trade name AP-88 or the particulate precursor SAP prior to surface X-linking was employed. AP-88 is a network X-linked sodium polyacrylate made by solvent polymerization from an aqueous acrylic acid solution including 2 network X-linking agents. AP-88 has a neutralization degree of 70 mol %.

Example 1

The particulate precursor SAP was screened to 95 to 850 micrometers, and then, 200 grams were mixed with 2 grams of powdery kaolin (NeoGen 2000) in a Bausch bread kneader for 5 minutes at speed 3. An aqueous solution containing 20% by weight of ethylene carbonate (surface X-linking agent) was then added by spraying. The ethylene carbonate was calculated to be 0.5% by weight based on dry SAP. The mixture was heated in an oven at 190° C. for 35 minutes, cooled, and screened to a PSD ranging from about 150 to 850 micrometers. The particles of the screened resultant particulate material composition (of AP-88 and kaolin) were of such a size that less than 40% passed through a U.S. Standard 50 mesh sieve (300 μm size openings).

Example 2

The particulate precursor SAP according to Example 1 was mixed with kaolin and surface X-linked in the same manner as in Example 1, except that 6 grams of powdery kaolin (NeoGen 2000) were used.

Example 3

The particulate precursor SAP according to Example 1 was mixed with kaolin and surface X-linked in the same manner as in Example 1, except that 1 gram of powdery kaolin (NeoGen DGH) was used.

Example 4

The particulate precursor SAP according to Example 1 was mixed with kaolin and surface X-linked in the same manner as in Example 1, except that 4 grams of powdery kaolin (NeoGen DGH) were used.

Example 5

The particulate precursor SAP according to Example 1 was mixed with an aqueous slurry containing 6.25% by weight of ethylene carbonate (surface X-linking agent) and 25% by weight of kaolin (NeoGen DGH) using an atomized spraying system (Nordson Pump/Airless Gun®, Model 25B with Nordson Cross-Cut® Nozzle). The final ethylene carbonate and kaolin concentrations were 0.5% and 2%, respectively, both based on dry SAP. The mixture was then blended for 2 hours, transferred to an oven and heated at 190° C. for 25 minutes to complete the surface X-linking treatment. The final particulate material composition (of AP-88 and kaolin) was sieved to a PSD ranging from about 150 to 850 micrometers.

Example 6

The particulate precursor SAP according to Example 1 was mixed with an aqueous solution containing 50% by weight of ethylene carbonate. The final ethylene carbonate concentration was 0.6% based on dry SAP. The mixture was then transferred to a conveyor where it was heated from 65° C. to 185° C. in 1 hour to complete the surface X-linking treatment.

After cooling, the AP-88 was sprayed with an aqueous slurry containing 50% kaolin (NeoGen DGH), to provide a calculated kaolin concentration of 3% based on dry AP-88 weight. The particulate material composition (of AP-88 and kaolin) thus obtained was then sieved to a PSD ranging from about 150 to 850 micrometers.

Example 7

The particulate precursor AP-88 that was surface X-linked as described in Example 6 was cooled, and then blended with a 50% solution of kaolin to provide a final 2% by weight of kaolin (NeoGen DGH), based on dry AP-88 weight. The resultant particulate material composition (of AP-88 and kaolin) was sieved to a PSD ranging from about 150 to 850 micrometers.

Example 8

The particulate AP-88 was mixed with an aqueous slurry of kaolin using an atomized spraying system (Nordson Pump/Airless Gun®, Model 25B with Nordson Cross-Cut® Nozzle). The final kaolin (NeoGen DGH) concentration was 2.5% based on dry AP-88. The final particulate material composition was sieved to a PSD ranging from about 150 to 850 micrometers.

For each of Examples 1–8, the resultant particulate material compositions of inorganic kaolin clay powder and SAP (having the % indicated below as passing through a U.S. Standard 50 mesh sieve) were tested for CRC, AUL, anti-caking, and dust rating.

The results are summarized in Table A below.

Examples 9–14 (Comparisons)

For each of Comparison Examples 9–13, the respective procedures of each of Examples 1–5 were repeated, except that (1) the sample of SAP was selected such that it had the PSD indicated below and (2) 1% of fine amorphous silica (sold by Nippon Aerosil of Japan under the trade name AEROSIL 200) was used instead of kaolin. For Comparison Example 14, the procedure of Example 6 was repeated to make a composition of kaolin and SAP, except that the

TABLE A

| Example No. | PSD of SAP | kaolin (wt %) | % of composition (SAP + kaolin) passing 50 mesh | CRC (g/g) | 0.9 AUL (g/g) | Light 3 hr anti-caking (%) | Moderate 6 hr anti-caking (%) | Heavy 15 hr anti-caking (%) | Very Heavy 24 hr anti-caking (%) | Dust Rating |
|---|---|---|---|---|---|---|---|---|---|---|
| AP-88 | Bulk | 0 | 21 (SAP only, no kaolin) | 32 | 20 | 30 | 13 | 0.1 | 0 | 2 |
| 1 | Bulk | NeoGen 2000, 1% | 10 | 35 | 17 | 100 | 98 | 96 | 88 | 1 |
| 2 | Bulk | NeoGen 2000, 3% | 9 | 32 | 16 | 100 | 100 | 100 | 100 | 2 |
| 3 | Bulk | NeoGen 2000, 0.5% | 5 | 35 | 18 | 97 | 85 | 68 | 99 | 1 |
| 4 | Bulk | NeoGen DGH, 2% | 5 | 32 | 18 | 100 | 99 | 100 | 99 | 1 |
| 5 | Bulk | NeoGen DGH, 2% | 15 | 32 | 18 | 100 | 100 | 100 | 99 | 1 |
| 6 | Bulk | NeoGen DGH, 3% | 4 | 30 | 19 | 100 | 100 | 99 | 98 | 2 |
| 7 | Bulk | NeoGen DGH, 2% | 11 | 31 | 21 | 100 | 97 | 91 | 75 | 1 |
| 8 | Bulk | NeoGen DGH, 2.5% | 27 | 31 | 21 | 100 | 100 | 99 | 99 | 1 |

As can be seen from Table A, all samples of SAP+kaolin exhibited the preferred result of about 90% or higher of for the light anti-caking property (3 hour test) and the desired result of about 85% or higher for the moderate anti-caking property (6 hour test). Also, most samples of SAP+kaolin (except for the sample of SAP+NeoGen DGH at 0.5%) exhibited the preferred and/or desired result for the heavy anti-caking property (15 hour test) and the very heavy anti-caking property (24 hour test).

sample of SAP was selected such that it had the PSD indicated below.

The resultant particulate material compositions of inorganic powder and SAP (having the % indicated below as passing through a U.S. Standard 50 mesh sieve) were tested for CRC, AUL, anti-caking, and dust rating.

The results are summarized in Table B below.

TABLE B

| Example No. | PSD of SAP mesh and microns | Inorganic Powder Additive (%) | % of composition (SAP + inorganic powder) passing 50 mesh | CRC (g/g) | 0.9 AUL (g/g) | Light 3 hr anti-caking (%) | Moderate 6 hr anti-caking (%) | Heavy 15 hr anti-caking (%) | Very Heavy 24 hr anti-caking (%) | Dust rating |
|---|---|---|---|---|---|---|---|---|---|---|
| Comparison 9 | Bulk −20/+325 and 45 μm to 850 μm | Aerosil 200, 1% | 23 | 33 | 16 | 80 | 68 | 48 | 23 | 1 |
| Comparison 10 | −30/+325 and 45 μm to 600 μm | Aerosil 200, 1% | 33 | 33 | 18 | 89 | 55 | 40 | 15 | 2 |
| Comparison 11 | −40/+325 and | Aerosil 200, 1% | 67 | 30 | 16 | 55 | 45 | 0.1 | 0 | 3 |

TABLE B-continued

| Example No. | PSD of SAP mesh and microns | Inorganic Powder Additive | % of composition (SAP + inorganic powder) passing 50 mesh | CRC (g/g) | 0.9 AUL (g/g) | Light 3 hr anti-caking (%) | Moderate 6 hr anti-caking (%) | Heavy 15 hr anti-caking (%) | Very Heavy 24 hr anti-caking (%) | Dust rating |
|---|---|---|---|---|---|---|---|---|---|---|
| Comparison 12 | 45 μm to 425 μm −50/+325 and 45 μm to 300 μm | Aerosil 200, 1% | 100 | 28 | 19 | 53 | 36 | 1.1 | 0 | 3–4 |
| Comparison 13 | −50/+100 and 150 μm to 300 μm | Aerosil 200, 1% slurry | 100 | 25 | 18 | 0 | 0 | 0.2 | 0 | 1 |
| Comparison 14 | −50/+100 and 150 μm to 300 μm | NeoGen DGH, 2% | 100 | 27 | 17 | 81 | 42 | 39 | 21 | 4 |

The above-discussed U.S. Pat. No. 5,419,956 teaches both the use of (A) AEROSIL 200 as the inorganic powder and (B) compositions of SAP+inorganic powder where over 70% of the composition passed through a U.S. Standard 50 mesh sieve. When AEROSIL 200 was used as the inorganic powder is illustrated in Comparison Examples 9–13 in Table B. When over 70% of the composition of SAP+inorganic powder passed through a U.S. Standard 50 mesh sieve is illustrated by Comparison Examples 12–14 in Table B. As can be seen in Table B, the following occurred from the use of (A) AEROSIL 200 or (B) compositions where over 70% passed through a U.S. Standard 50 mesh sieve. The resultant anti-caking performance was unsatisfactory and far below both the desirable about 85% or higher and the preferred about 90% or higher for the moderate anti-caking property (6 hour test), the heavy anti-caking property (15 hour test), and the very heavy anti-caking property (24 hour test) for the particulate material compositions of kaolin+SAP in accordance with the present invention. Also, all Comparisons were below the preferred about 90% or higher for the light anti-caking property (3 hour test) for the particulate material compositions of kaolin+SAP in accordance with the present invention.

Example 15 and Comparison Example 16 (Cores of SAP and Cellulosic Fluff Made by Air-Laid Process)

The inventive particulate material composition (of 2.5% NeoGen DGH kaolin and AP-88 SAP) made as described above in Example 8 and also AP-88 alone as a control were each respectively employed in a conventional air-laid process, using a laboratory scale Dan-Web machine, to make a core with cellulosic fiber. The basis weight of each core was 0.084 g/cm2, and each had a composition (NeoGen DGH+AP-88) to fiber ratio, or an AP-88 to fiber ratio, of 35:65. As is well known, such cores are useful in absorbent articles, such as sanitary napkins or disposable diapers.

Each absorbent core was then tested with 0.9% by weight aqueous saline for performance results of acquisition time and multiple rewet.

No statistically significant difference was seen between the core made with the inventive composition (NeoGen DGH+AP-88) as compared to the core made with AP-88. Thus, the presence of kaolin does not interfere with the performance of the SAP in an end use product, such as a sanitary napkin or a throwaway diaper.

The results for an insult amount of 100 ml repeated 3 times are summarized below in Table C.

TABLE C

| | Example No. 15 NeoGen DGH and AP-88 | Comparison Example No. 16 AP-88 |
|---|---|---|
| Acquisition Time (seconds) | | |
| Time 1 | 37 | 36 |
| Time 2 | 80 | 91 |
| Time 3 | 136 | 131 |
| Multiple Rewet (grams) | | |
| Rewet 1 | 0.2 | 0.2 |
| Rewet 2 | 0.4 | 0.3 |
| Rewet 3 | 0.8 | 0.6 |

It will be understood that various details of the invention may be changed without departing from the scope of the invention. Furthermore, the foregoing description is for the purpose of illustration only, and not for the purpose of limitation—the invention being defined by the claims.

What is claimed is:

1. A particulate material composition comprising an inorganic powder intermixed with particles of superabsorbent polymer, said polymer particles being of such size that less than about 60% of said polymer particles, by weight, will pass through a U.S. Standard 50 mesh sieve with 300 micrometer openings, and wherein the composition exhibits anti-caking characteristics in that more than about 90% of the composition particles, by weight, will pass through a U.S. Standard 12 mesh sieve with 1700 micrometer openings after at least about 3 hours at about 36±3° C. and about 77±3% relative humidity.

2. The composition of claim 1, wherein less than about 50% of said polymer particles by weight will pass through a U.S. Standard 50 mesh sieve with 300 micrometer openings.

3. The composition of claim 2, wherein less than about 40% of said polymer particles by weight will pass through a U.S. Standard 50 mesh sieve with 300 micrometer openings.

4. The composition of claim 1, wherein said inorganic powder is selected from the group consisting of clays.

5. The composition of claim 4, wherein said clay is a kaolin clay.

6. The composition of claim 1, wherein said inorganic powder comprises inorganic powder particles of less than about 5 micrometers in average size.

7. The composition of claim 6, wherein said inorganic powder particles are of less than about 3 micrometers in average size.

8. The composition of claim 7, wherein said inorganic powder particles are of less than about 0.8 micrometer in average size.

9. The composition of claim 1, wherein said inorganic powder is mixed with said polymer particles in an amount of between about 0.2% to about 10% by weight of said polymer particles.

10. The composition of claim 9, wherein said inorganic powder is mixed with said polymer particles in an amount of between about 0.5% to about 7% by weight of said polymer particles.

11. The composition of claim 10, wherein said inorganic powder is mixed with said polymer particles in an amount of between about 0.9% to about 5.5% by weight of said polymer particles.

12. The composition of claim 1, wherein said polymer is selected from the group consisting of hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, acrylamido-methylpropane-sulfonic acid terpolymers, acrylic acid polymers, methacrylic acid polymers, network cross-linked products of any of the foregoing, and combinations thereof.

13. The composition of claim 1, wherein at least a portion of said polymer particles is surface cross-linked.

14. The composition of claim 1, wherein the composition exhibits anti-caking characteristics in that more than about 90% of said composition particles, by weight, will pass through a U.S. Standard 12 mesh sieve with 1700 micrometer openings after at least about 6 hours at about 36±3° C. and about 77±3% relative humidity.

15. The composition of claim 14, wherein the composition exhibits anti-caking characteristics in that more than about 90% of said composition particles, by weight, will pass through a U.S. Standard 12 mesh sieve with 1700 micrometer openings after at least about 15 hours at about 36±3° C. and about 77±3% relative humidity.

16. The composition of claim 15, wherein the composition exhibits anti-caking characteristics in that more than about 90% of said composition particles, by weight, will pass through a U.S. Standard 12 mesh sieve with 1700 micrometer openings after at least about 24 hours at about 36±3° C. and about 77±3% relative humidity.

17. The composition of claim 1, wherein the composition exhibits dust reduction characteristics.

18. An absorbent article comprising a particulate material composition of an inorganic powder intermixed with particles of superabsorbent polymer, said polymer particles being of such size that less than about 60% of said polymer particles, by weight, will pass through a U.S. Standard 50 mesh sieve with 300 micrometer openings, and wherein the particulate material composition, prior to incorporation into the article, exhibits anti-caking characteristics in that more than about 90% of the composition particles, by weight, will pass through a U.S. Standard 12 mesh sieve with 1700 micrometer openings after at least about 3 hours at about 36±3° C. and about 77±3% relative humidity.

19. The absorbent article of claim 18, wherein less than about 50% of said polymer particles by weight, will pass through a U.S. Standard 50 mesh sieve with 300 micrometer openings.

20. The absorbent article of claim 19, wherein less than about 40% of said polymer particles, by weight, will pass through a U.S. Standard 50 mesh sieve with 300 micrometer openings.

21. The absorbent article of claim 18, wherein said inorganic powder is selected from the group consisting of clays.

22. The absorbent article of claim 21, wherein said clay is a kaolin clay.

23. The absorbent article of claim 18, wherein said inorganic powder comprises inorganic powder particles of less than about 5 micrometers in average size.

24. The absorbent article of claim 23, wherein said inorganic powder particles are of less than about 3 micrometers in average size.

25. The absorbent article of claim 24, wherein said inorganic powder particles are of less than about 0.8 micrometer in average size.

26. The absorbent article of claim 18, wherein said inorganic powder is mixed with said polymer particles in an amount of between about 0.2% to about 10% by weight of said polymer particles.

27. The absorbent article of claim 26, wherein said inorganic powder is mixed with said polymer particles in an amount of between about 0.5% to about 7% by weight of said polymer particles.

28. The absorbent article of claim 18, wherein said inorganic powder is mixed with said polymer particles in an amount of between about 0.9% to about 5.5% by weight of said polymer particles.

29. The absorbent article of claim 18, wherein said polymer is selected from the group consisting of hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, acrylamido-methylpropane-sulfonic acid terpolymers, acrylic acid polymers, methacrylic acid polymers, network cross-linked products of any of the foregoing, and combinations thereof.

30. The absorbent article of claim 18, wherein at least a portion of said polymer particles is surface cross-linked.

31. The absorbent article of claim 18, wherein the particulate material composition, prior to incorporation into the article, exhibits anti-caking characteristics in that more than about 90% of said composition particles, by weight, will pass through a U.S. Standard 12 mesh sieve with 1700 micrometer openings after at least about 6 hours at about 36±3° C. and about 77±3% relative humidity.

32. The absorbent article of claim 31, wherein the particulate material composition, prior to incorporation into the article, exhibits anti-caking characteristics in that more than about 90% of said composition particles, by weight, will pass through a U.S. Standard 12 mesh sieve with 1700 micrometer openings after at least about 15 hours at about 36±3° C. and about 77±3% relative humidity.

33. The absorbent article of claim 32, wherein the particulate material composition, prior to incorporation into the article, exhibits anti-caking characteristics in that more than about 90% of said composition particles, by weight, will pass through a U.S. Standard 12 mesh sieve with 1700 micrometer openings after at least about 24 hours at about 36±3° C. and about 77±3% relative humidity.

34. The absorbent article of claim 18, wherein the particulate material composition, prior to incorporation into the article, exhibits dust reduction characteristics.

35. A method for providing anti-caking characteristics to particles of superabsorbent polymer, said method comprising:
(A) providing superabsorbent polymer particles of such size that less than about 60% of the polymer particles, by weight, will pass through a U.S. Standard 50 mesh sieve with 300 micrometer openings;
(B) mixing an inorganic powder with the polymer particles in an amount of between about 0.2% to about 10% by weight of the polymer particles, to create a particulate material composition; and
(C) achieving anti-caking characteristics in that more than about 90% of the composition particles, by weight, will pass through a U.S. Standard 12 mesh sieve with 1700 micrometer openings after at least about 3 hours at about 36±3° C. and about 77±3% relative humidity.

36. The method of claim 35, wherein less than about 50% of said polymer particles by weight will pass through a U.S. Standard 50 mesh sieve with 300 micrometer openings.

37. The method of claim 36, wherein less than about 40% of said polymer particles by weight will pass through a U.S. Standard 50 mesh sieve with 300 micrometer openings.

38. The method of claim 35, wherein said inorganic powder is selected from the group consisting of clays.

39. The method of claim 38, wherein said clay is a kaolin clay.

40. The method of claim 35, wherein said inorganic powder comprises inorganic powder particles of less than about 5 micrometers in average size.

41. The method of claim 40, wherein said inorganic powder particles are of less than about 3 micrometers in average size.

42. The method of claim 41, wherein said inorganic powder particles are of less than about 0.8 micrometer in average size.

43. The method of claim 35, wherein said inorganic powder is mixed with said polymer particles in an amount of between about 0.5% to about 7% by weight of said polymer particles.

44. The method of claim 43, wherein said inorganic powder is mixed with said polymer particles in an amount of between about 0.9% to about 5.5% by weight of said polymer particles.

45. The method of claim 35, wherein anti-caking characteristics are achieved in that more than about 90% of said composition particles, by weight, will pass through a U.S. Standard 12 mesh sieve with 1700 micrometer openings after at least about 6 hours at about 36±3° C. and about 77±3% relative humidity.

46. The method of claim 45, wherein anti-caking characteristics are achieved in that more than about 90% of said composition particles, by weight, will pass through a U.S. Standard 12 mesh sieve with 1700 micrometer openings after at least about 15 hours at about 36±3° C. and about 77±3% relative humidity.

47. The method of claim 46, wherein anti-caking characteristics are achieved in that more than about 90% of said composition particles, by weight, will pass through a U.S. Standard 12 mesh sieve with 1700 micrometer openings after at least about 24 hours at about 36±3° C. and about 77±3% relative humidity.

48. The method of claim 35, wherein the polymer is selected from the group consisting of hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, acrylamido-methylpropane-sulfonic acid terpolymers, acrylic acid polymers, methacrylic acid polymers, network cross-linked products of any of the foregoing, and combinations thereof.

49. The method of claim 35, wherein at least a portion of said polymer particles is surface cross-linked.

50. The method of claim 35, further including achieving dust reduction characteristics for the composition particles.

51. A method for providing anti-caking characteristics to a particulate material composition in an absorbent article, said method comprising:
(A) providing superabsorbent polymer particles of such size that less than about 60% of the polymer particles, by weight, will pass through a U.S. Standard 50 mesh sieve with 300 micrometer openings;
(B) mixing an inorganic powder with the polymer particles in an amount of between about 0.2% to about 10% by weight of the polymer particles, to create the particulate material composition;
(C) achieving anti-caking characteristics in that more than about 90% of the composition particles, by weight, will pass through a U.S. Standard 12 mesh sieve with 1700 micrometer openings after at least about 3 hours at about 36±3° C. and about 77±3% relative humidity; and
(D) forming an absorbent article from the particulate material composition of step (C).

52. The method of claim 51, wherein less than about 50% of said polymer particles, by weight, will pass through a U.S. Standard 50 mesh sieve with 300 micrometer openings.

53. The method of claim 52, wherein less than about 40% of the polymer particles, by weight, will pass through a U.S. Standard 50 mesh sieve with 300 micrometer openings.

54. The method of claim 52, wherein the inorganic powder is selected from the group consisting of clays.

55. The method of claim 54, wherein said clay is a kaolin clay.

56. The method of claim 51, wherein said inorganic powder comprises inorganic powder particles of less than about 5 micrometers in average size.

57. The method of claim 56, wherein said inorganic powder particles are of less than about 3 micrometers in average size.

58. The method of claim 57, wherein said inorganic powder particles are of less than about 0.8 micrometer in average size.

59. The method of claim 51, wherein said inorganic powder is mixed with said polymer particles in an amount of between about 0.5% to about 7% by weight of said polymer particles.

60. The composition of claim 59, wherein said inorganic powder is mixed with said polymer particles in an amount of between about 0.9% to about 5.5% by weight of said polymer particles.

61. The method of claim 51, wherein anti-caking characteristics are achieved in that more than about 90% of said composition particles, by weight, will pass through a U.S. Standard 12 mesh sieve with 1700 micrometer openings after at least about 6 hours at about 36±3° C. and about 77±3% relative humidity.

62. The method of claim 61, wherein anti-caking characteristics are achieved in that more than about 90% of said composition particles, by weight, will pass through a U.S. Standard 12 mesh sieve with 1700 micrometer openings after at least about 15 hours at about 36±3° C. and about 77±3% relative humidity.

63. The method of claim 62, wherein anti caking characteristics are achieved in that more than about 90% of said composition particles, by weight, will pass through a U.S. Standard 12 mesh sieve with 1700 micrometer openings after at least about 24 hours at about 36±3° C. and about 77±3% relative humidity.

64. The method of claim 51, wherein the polymer is selected from the group consisting of hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, acrylamido-methylpropane-sulfonic acid terpolymers, acrylic acid polymers, methacrylic acid polymers, network cross-linked products of any of the foregoing, and combinations thereof.

65. The method of claim 51, wherein at least a portion of said polymer particles is surface cross-linked.

66. The method of claim 51, wherein step (D) includes forming the absorbent article by mixing the particulate material composition with a fibrous component.

67. The method of claim 51, further including achieving dust reduction characteristics for the composition particles.

* * * * *